United States Patent
Landis et al.

(10) Patent No.: US 9,933,354 B2
(45) Date of Patent: Apr. 3, 2018

(54) METHOD FOR MANUFACTURING A SUBSTRATE FOR SURFACE-ENHANCED RAMAN SPECTOGRAPHY AND SUBSTRATE

(71) Applicant: COMMISSARIAT A L'ENERGIE ATOMIQUE ET AUX ENERGIES ALTERNATIVES, Paris (FR)

(72) Inventors: Stefan Landis, Tullins (FR); Vincent Reboud, Paris (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 92 days.

(21) Appl. No.: 14/988,064

(22) Filed: Jan. 5, 2016

(65) Prior Publication Data
US 2016/0195468 A1    Jul. 7, 2016

(30) Foreign Application Priority Data
Jan. 5, 2015    (FR) ...................................... 15 50012

(51) Int. Cl.
G01N 21/65    (2006.01)
G01N 21/01    (2006.01)
(Continued)

(52) U.S. Cl.
CPC ............. *G01N 21/01* (2013.01); *B82Y 30/00* (2013.01); *G01J 3/44* (2013.01); *G01N 21/658* (2013.01);
(Continued)

(58) Field of Classification Search
CPC ................. G01N 21/658; G01N 21/65; G01N 2021/653; G01N 2021/655;
(Continued)

(56) References Cited

U.S. PATENT DOCUMENTS 7,483,130 B2 *  1/2009  Baumberg ........... G01N 21/658
                                                         356/301
2006/0119853 A1 *  6/2006  Baumberg ........... G01N 21/658
                                                         356/445
(Continued)

FOREIGN PATENT DOCUMENTS

JP    2013-232444 A    11/2013
KR    10-2011-0097354 A    8/2011

OTHER PUBLICATIONS

Kyoung Hwan Kim, Youn-Kyoung Baek, Hwan-Jin Jeon, Mohan Srinivasarao, and Hee-Tae Jung, "Cylindrical posts of Ag/SiO2/Au multi-segment layer patterns for highly efficient surface enhanced Raman scattering," Nanotechnology, vol. 23, No. 31, Published Jul. 17, 2012.*

(Continued)

*Primary Examiner* — Kara E Geisel
*Assistant Examiner* — Violeta A Prieto
(74) *Attorney, Agent, or Firm* — Pillsbury Winthrop Shaw Pittman LLP (57)    ABSTRACT

A substrate for surface-enhanced Raman spectography includes a support including an upper surface; a multilayer deposited on the upper surface, with the multilayer including at least two metal layers separated from each other by an intermediate layer, the intermediate layer being selectively etchable with respect to the metal layers, the multilayer being passed through by at least one trench delimited by ends of each one of the layers of the multilayer, each end of each intermediate layer being set back with respect to the end of each metal layer adjacent to the intermediate layer in such a way that the ends of two successive metal layers form metal pins separated by a cavity; a reflective optical system arranged in each trench, with the reflective optical system being arranged to direct inside the cavities an incident light (Continued)

arriving according to an angle with respect to the upper surface of the support.

15 Claims, 4 Drawing Sheets

(51) Int. Cl.
    *B82Y 30/00*      (2011.01)
    *G01J 3/44*      (2006.01)
    *B82Y 15/00*      (2011.01)
    *B82Y 20/00*      (2011.01)

(52) U.S. Cl.
    CPC .............. *B82Y 15/00* (2013.01); *B82Y 20/00* (2013.01); *G01N 2201/068* (2013.01)

(58) Field of Classification Search
    CPC ............. G01N 2021/656; G01N 21/01; G01N 2201/068; G01J 3/44
    See application file for complete search history.

(56) References Cited

U.S. PATENT DOCUMENTS

| | | | | |
|---|---|---|---|---|
| 2006/0164635 A1* | 7/2006 | Islam | .................... | G01N 21/658 356/301 |
| 2009/0141355 A1* | 6/2009 | Thomas | ................. | B82Y 20/00 359/576 |
| 2009/0273779 A1* | 11/2009 | Baumberg | ........... | G01N 21/658 356/301 |
| 2011/0109902 A1* | 5/2011 | Lin | ...................... | G01N 21/658 356/301 |
| 2011/0222179 A1* | 9/2011 | Monadgemi | ..... | B29D 11/00596 359/850 |
| 2011/0267609 A1 | 11/2011 | Wu et al. | | |
| 2012/0119315 A1* | 5/2012 | Ou | ...................... | G01N 21/658 257/431 |
| 2016/0195476 A1* | 7/2016 | Landis | ................... | C23C 14/24 356/244 |

OTHER PUBLICATIONS

Lin, T.-R., et al., "Coating effect on optical resonance of plasmonic nanobowtie antenna," Applied Physics Letters 97, 063106, 2010.

Ou, F.S., et al., "Hot-Spot Engineering in Polygonal Nanofinger Assemblies for Surface Enhanced Raman Spectroscopy," Nano Letters 2011, 11, pp. 2538-2542.

Choi, S., et al., "Ultradense gold nanostructures fabricated using hydrogen silsesquioxane resist and applications for surface-enhanced Raman spectroscopy," Journal of Vacuum Science & Technology B 27, pp. 2640-2643, 2009.

Zhang, Z., et al., "Manipulating Nanoscale Light Fields with the Asymmetric Bowtie Nano-Colorsorter," Nano Letters, vol. 9, No. 12, 2009, pp. 4505-4509.

French Search Report as issued in French Patent Application No. 1550012, dated Jul. 24, 2015.

Li, Z., et al., "Optical properties of ordered Dot-on-Plate nanosandwich arrays," Microelectronic Engineering, vol. 127, Apr. 12, 2014, pp. 34-39.

* cited by examiner

METHOD FOR MANUFACTURING A SUBSTRATE FOR SURFACE-ENHANCED RAMAN SPECTOGRAPHY AND SUBSTRATE

CROSS-REFERENCE TO RELATED APPLICATIONS

This application claims priority to French Patent Application No. 1550012, filed Jan. 5, 2015, the entire content of which is incorporated herein by reference in its entirety.

FIELD

The field of the invention is that of methods for manufacturing substrates that can be used to implement methods of surface-enhanced Raman spectography (SERS). The invention also relates to a substrate for surface-enhanced Raman spectography.

BACKGROUND

Surface-enhanced Raman spectography (SERS) is one of the most promising detection techniques for identifying and characterising molecules. This technique consists in depositing the molecules of interest on a substrate that has a rough metal surface. The metal surface whereon the molecules of interest are fixed is then illuminated by a monochromatic light. The molecules then emit a Raman signal characteristic of these molecules, which makes them able to be detected and identified.

However the Raman signal emitted by the molecules has an intensity that is much less than the intensity of the monochromatic light with which the molecules were illuminated.

In order to overcome this problem, it has been observed that the roughness of the metal surface of the substrate that carries the molecules of interest makes it possible to enhance the Raman signal emitted by the molecules of interest thanks to the excitation of localised plasmons of the metal (enhancement via electromagnetic effect) and by transfer of charges between the metal and the molecule adsorbed (chemical effect). This enhancement makes it possible as such to specifically detect adsorbed samples with extremely low concentrations and/or over very short periods of time.

This enhancement can be accomplished thanks to "hot spots". These hot spots are zones of the substrate where the electromagnetic field is localised and intense. For this, hot spots generally have dimensions that are less than the wavelength of the monochromatic light.

Prior art as such knows methods that make it possible to carry out hot spots on the surface of a substrate. These hot spots can be formed by cavities or by point effects. As such, the document Appl. Phys. Lett. 97, 063106 2010, Nanoletters, 9, 4505, 2009 describes hot spots formed by points. The document Nano Lett. 11, 2538, 2011; J. Vac. Sci. Technol. B 27, 2640 (2009) describes hot spots formed by cavities. However, the methods for forming hot spots of prior art use structuring technologies that can reach very high spatial resolutions and they are therefore complex and very expensive. Furthermore, they do not generally make it possible to produce substrates that have a high density of hot spots, in such a way that the increase in the light intensity emitted by the molecules of interest is limited.

SUMMARY

An aspect of the invention aims to overcome the disadvantages of prior art by proposing a method for manufacturing a substrate for surface-enhanced Raman spectography that is easy to implement, and which allows for a constant increase in the light intensity emitted by the molecules over the whole of the substrate.

Another aspect of the invention is to propose a method for manufacturing a substrate for surface-enhanced Raman spectography that can be reproduced and that is reliable, that allows for a substantial increase in the light intensity emitted by the molecules of interest and which has a high density of hot spots.

Another aspect of the invention is to propose a method for manufacturing a substrate for surface-enhanced Raman spectography that makes it possible to simultaneously carry out a large number of identical substrates.

To do this, a first aspect of the invention relates to a method for manufacturing a substrate for surface-enhanced Raman spectography, with the method comprising the following steps:

(a) depositing of a multilayer on an upper surface of a support, with the multilayer comprising at least two metal layers separated from each other by an intermediate layer, with the intermediate layer able to be etched selectively with respect to the metal layers;

(b) etching of the multilayer in such a way as to form at least one trench through the multilayer, the trench being delimited by ends of each one of the layers of the multilayer;

(c) selective etching of a portion of each end of each intermediate layer in such a way as to form a cavity between the ends of two successive metal layers in such a way that the ends of two successive metal layers form metal pins separated by a cavity;

(d) formation of a reflective optical system in each trench, with the reflective optical system being arranged to direct inside the cavities an incident light arriving according to an angle α with respect to the upper surface of the support.

The reflective optical system is configured to direct inside the cavities an incident light arriving according to an angle α with respect to the upper surface of the support. The reflective optical system does not produce any surface-enhanced Raman spectography. Consequently, only the direction of the incident light is modified when it arrives on the reflective optical system. In particular, the reflective optical system does not filter wavelengths. The reflective optical system reflects all of the wavelengths that it has received in the cavity. It absorbs none of them. The reflective optical system does not diffuse light but reflects it.

The reflective optical system also makes it possible to redirect to the system for collecting the light diffused (SERS) by the cavities. There is therefore a double usage:
It sends the light in the cavities;
it also reflects the light emitted from the cavities to the light detector.

The method therefore proposes to deposit a multilayer on a flat surface. A cut is then made locally in the thickness of this multilayer in such a way as to form at least one trench in the multilayer. A partial selective withdrawal of each intermediate layer is then carried out. Metal nanostructures are as such obtained separated by spaces of which the dimensions can be controlled perfectly by controlling the thickness of the intermediate layer deposited. An optical system is then formed in the trench so as to direct an incident light arriving according to an angle α with respect to the upper surface of the support in the cavities formed. Indeed, by supposing for example that the incident light arrives according to a direction normal to the substrate, the cavities formed between the metal pins are not directly accessible to this incident light. It is therefore beneficial to add an optical system in such a way that the incident light is deviated so that it penetrates into the cavities. This optical system will also make it possible to recover the electromagnetic signal generated by the substrate on the side of the multilayer. Molecules to be detected can then be deposited on the surface of the substrate. A substrate for surface-enhanced Raman spectography allowing for a localised reinforcing of the electromagnetic field when it is subjected to an incident electromagnetic radiation at a predefined wavelength is as such obtained.

The method therefore makes it possible to very easily manufacture metal pins of nanometric dimensions separated by cavities of nanometric dimensions without resorting to aggressive etching methods. Furthermore, the width of the pins and of the cavities is controlled very well since it is determined by the thickness of the layers deposited. This thickness is easy to control.

The method then makes it possible to easily obtain a substrate that allows for a reinforcing of the electromagnetic field. The intensity of the electromagnetic field obtained thanks to the substrate formed as such can as such be between 10 times and several thousands of times greater than that obtained with the substrates of prior art.

The method according to an embodiment of the invention can also have one or several of the characteristics hereinafter taken individually or according to any technically permissible combination.

According to different embodiments:
  the steps (a), (b) and (c) can take place before the step (d), or
  the step (d) can take place before the steps (a), (b) and (c).

Indeed, as shall be seen in what follows, it can be decided to first carry out a trench of the multilayer, then to form an optical system in this trench or it can be decided to first form the optical system and to deposit the multilayer on either side of this optical system.

In an embodiment, the step (b) of etching the multilayer comprises the following steps:
  depositing a resin on the multilayer;
  etching the resin by lithography;
  etching of the multilayer by dry etching.

In an embodiment, the step of forming the optical system comprises a step of forming a microstructured pattern on the upper surface of the support. This microstructured pattern has in an embodiment walls that are inclined with respect to the surface of the sample, which makes it possible to direct the incident light in the cavities of the multilayer.

In an embodiment, the step of forming the optical system comprises a step of depositing a reflective layer on the microstructured pattern, which makes it possible to increase the quantity of incident light received by the cavities and inversely which makes it possible to increase the quantity of the Raman signal collected.

A second aspect of the invention relates to a substrate for surface-enhanced Raman spectography comprising:
  a support comprising an upper surface;
  a multilayer deposited on the upper surface of the support, with the multilayer comprising at least two metal layers separated from each other by an intermediate layer, with the intermediate layer able to be etched selectively with respect to the metal layers, with the multilayer being passed through by at least one trench delimited by the ends of each one of the layers of the multilayer, each end of each intermediate layer being set back with respect to the end of each metal layer adjacent to this intermediate layer in such a way that the ends of two successive metal layers form metal pins separated by a cavity;
  a reflective optical system arranged in each trench, with the reflective optical system being arranged to direct inside the cavities an incident light arriving according to an angle α with respect to the upper surface of the support.

Such a substrate comprises multiple hot spots on the cavities located between the ends of the metal layers, which makes it possible to substantially enhance the Raman signal emitted by the molecules of interest deposited on this substrate thanks to the excitation of localised plasmons of the metal (enhancement via electromagnetic effect). Such a substrate therefore makes it possible to increase the light intensity emitted by molecules of interest which are deposited on its surface in such a way that it allows for a faster detection of these molecules of interest.

The substrate according to the second aspect of the invention can have one or several of the characteristics hereinafter taken individually or according to any technically permissible combination.

The intermediate layer is in an embodiment a dielectric layer.

In an embodiment, the multilayer extends in parallel to the surface of the support, which makes it possible to deposit the multilayer directly on the surface of the support in such a way that the method of manufacturing the substrate is facilitated.

In an embodiment, each trench extends according to a direction normal to the surface of the support, which also makes it possible to facilitate the manufacture of the support.

In an embodiment, each cavity extends according to a direction parallel to the upper surface of the support.

In an embodiment, the reflective optical system comprises a microstructured pattern protruding from the upper surface of the support.

In an embodiment, the microstructured pattern is covered with a reflective layer.

BRIEF DESCRIPTION OF THE FIGURES

Other characteristics and benefits of the invention shall appear when reading the following detailed description, in reference to the annexed figures, which show.

DETAILED DESCRIPTION

FIGS. 1a to 1f show the various steps of a method according to an embodiment of the invention.

Figure 1A:
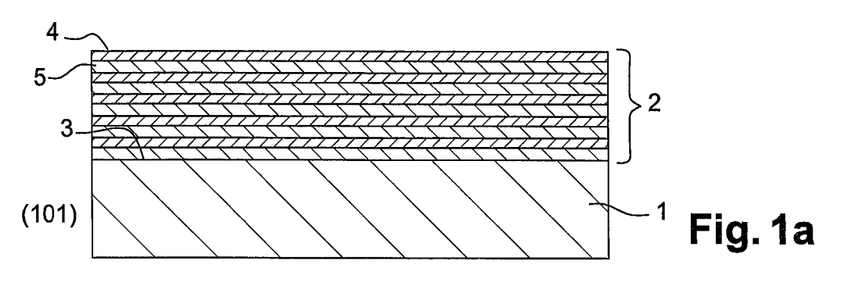
FIGS. 1a to 1f, steps of a method according to an embodiment of the invention.

In reference to FIG. 1a, the method comprises a first step 101 of depositing a multilayer 2 on an upper surface 3 of a support 1. According to various embodiments, the support 1 can be made of silicon, metal, glass. Moreover, the upper surface 3 can be covered by a layer of oxide, and in particular by a layer of silicon oxide.

The multilayer 2 comprises an alternating of metal layers 4 and of intermediate layers 5, with two successive metal layers 4 being separated by an intermediate layer 5.

The metal layers 4 are in an embodiment constituted of one of the following materials: gold, silver, copper, aluminium. According to various embodiments, the metal layers 4 can all be constituted of the same material, or they can be constituted of at least two by two with the same material. There can then be different pairs of metal layers in the multilayer which would make it possible to operate the device at different wavelengths. Moreover, the metal layers can all have the same thickness or they can have different thicknesses, which makes it possible to obtain a progressive index gradient. Indeed, by adjusting the thicknesses of each metal layer, the equivalent optical index of the multilayer can be varied between the optical index of the metal layers and that of the intermediate layers, as long as the sum of the thickness of a metal layer and of the thickness of an intermediate layer remains less than the incident wavelength. The substrate formed as such will then have resonances with several incident wavelengths.

Each metal layer has in an embodiment a thickness between 1 angstrom and 50 nm, in particular between 10 nm and 50 nm.

The intermediate layers 5 are constituted of a material that can be selectively etched with respect to the metal layers 4. According to various embodiments, the intermediate layers 5 can all be constituted of the same material, or they can be constituted of materials that differ from one another. In this latter case, all of the intermediate layers are in an embodiment constituted of a material that can be selectively etched with respect to the metal layers, either at the same time or one after the other with different methods. Having different cavity depths can then be considered and therefore adjust the operation and/or the resonance of the substrate obtained as such.

According to an embodiment, the intermediate layers 5 are constituted of a dielectric material. Indeed, dielectric materials do not absorb or absorb very little of the plasmon generated on the surface of the metal layers 4. The choice of dielectric material can be for example silicon oxide, alumina, hafnium oxide, silicon nitride, titanium oxide, etc. Moreover, the intermediate layers 5 can all have the same thickness or they can have different thicknesses, which makes it possible to obtain a progressive index gradient. The substrate formed as such will then have resonances with several incident wavelengths.

Each intermediate layer has in an embodiment a thickness between 1 angstrom and 20 nm, in particular between 10 nm and 20 nm.

It can also be considered to carry out the intermediate layers in metal materials. However, in this case, the depth of the cavities grooved into the intermediate layers should be more substantial than in the preceding embodiment, in such a way that the intermediate layers do not absorb the plasmon generated on the surface of the metal layers.

The layers of the multilayer are in an embodiment deposited by a compliant depositing method in such a way that the thickness of the multilayer is substantially the same over the entire upper surface of the support. For this, the layers of the multilayer can be deposited by physical vapour deposition, by electro deposition referred to as ECD, or by electrochemical deposition for example.

Figure 1B:
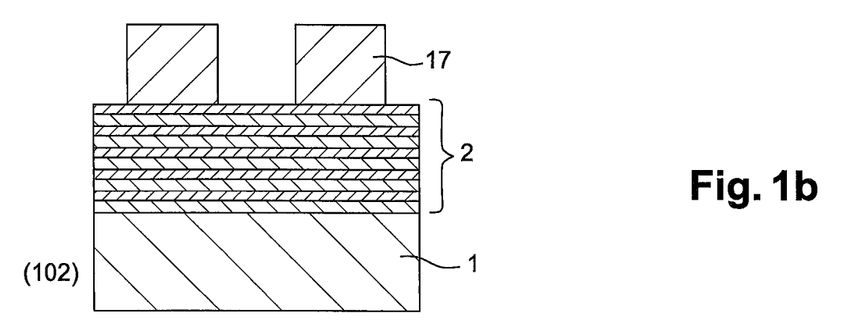
Figure 1C:
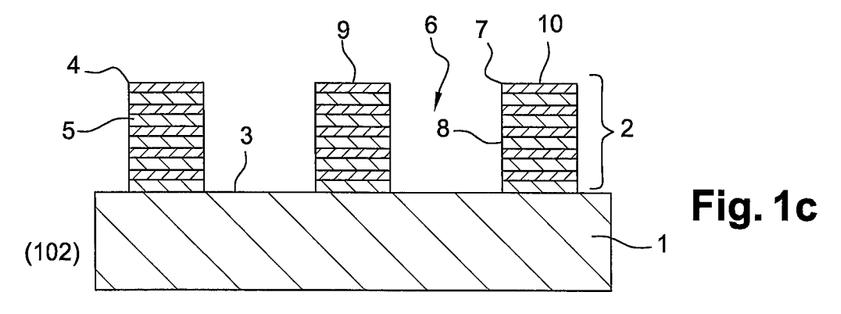

As shown in FIGS. 1b and 1c, the method then comprises a step 102 of etching the multilayer 2 in such a way as to form at least one trench 6 through the multilayer, with the trench 6 being delimited by ends 7, 8 of each one of the layers 4, 5 of the multilayer. The trench 6 therefore separates the multilayer 2 into at least two segments 9, 10 located on either side of the trench.

For this, the method can for example comprise a first step shown in FIG. 1b during which a resin mask 17 is formed on the multilayer. This resin mask 17 can for example be formed thanks to a step of depositing a layer of resin, for example via spin-coating, then by a step of lithography, for example optical, electronic, nanoprint, by AFM, etc. The multilayer 2 is then etched, for example by dry etching, through the mask. The step of dry etching of the multilayer can for example be carried out by a step of reactive-ion etching or by ionic machining. As shown in the FIG. 1c, at the end of this step 102 multilayer segments 9, 10 are obtained separated by des trenches 6, with each segment extending parallel to the upper surface 3 of the support 1. The trench 6 is delimited by the ends 7, 8 of the metal layers 4 and of the intermediate layers 5.

Figure 1D:
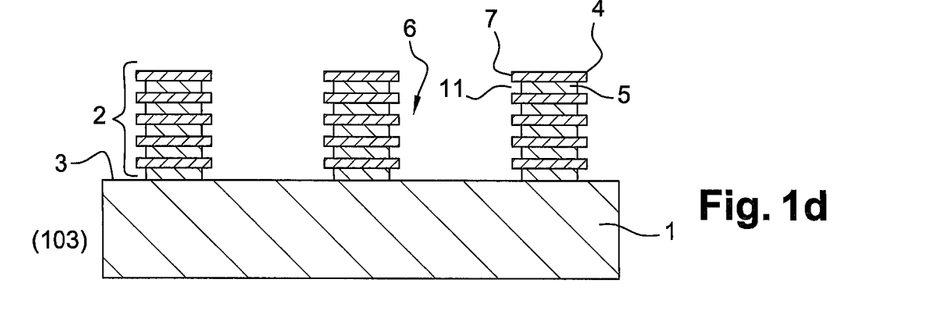

In reference to FIG. 1d, the method then comprises a step 103 of partial selective etching of a portion of the ends 8 of the intermediate layers 5 in such a way as to form cavities between the ends 7 of two successive metal layers. The ends 7 of the metal layers 4 thus form metal pins 7 separated by cavities 11. The cavities 11 extend parallel to the upper surface 3 of the support 1. Each cavity 11 has in an embodiment a depth between 1 angstrom and 200 nm, and in particular between 10 nm and 100 nm. This step of etching is partial so as to not affect the stability of the metal layers, and such that they do not collapse on one another.

Figure 1E:
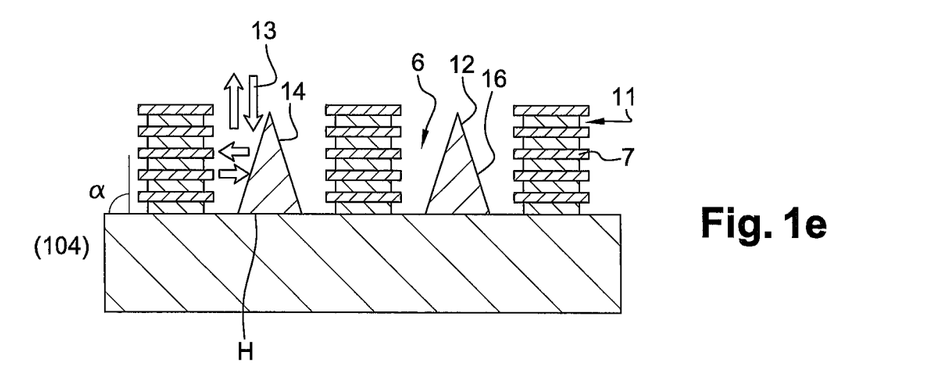

In reference to FIG. 1e, the method comprises a step 104 of forming an optical system 12 in each trench 6. Each optical system 12 is arranged in such a way as to direct inside the cavities 11 an incident light 13 arriving according to an angle α with respect to the upper surface of the support. In this embodiment, each optical system 12 is configured in such a way as to direct an incident light 13 arriving perpendicularly to the upper surface 3 of the support 1 in the cavities 11.

Figure 2A:
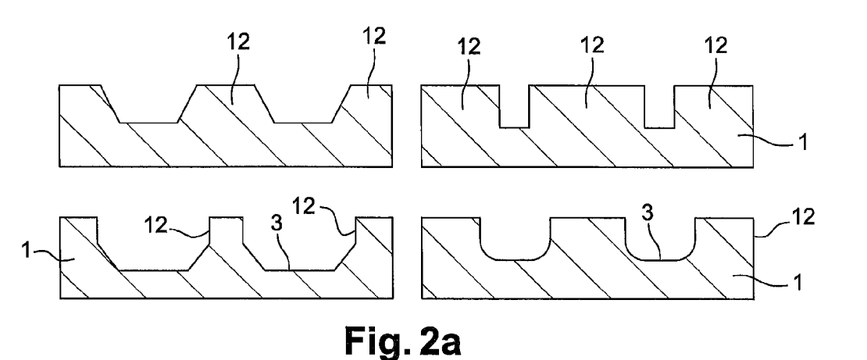
FIGS. 2a and 2b, alternatives steps of a method according to another embodiment of the invention.

For this, each optical system comprises a microstructured pattern 14 protruding from the upper surface 3 of the support. This microstructured pattern comprises in an embodiment a sidewall 16 forming an angle substantially equal to α/2, with α which is the angle formed between the incident light and the upper surface of the support. As such, in this embodiment, wherein each optical system is configured to redirect a light arriving perpendicularly to the surface of the support in the cavities 11, each microstructured pattern therefore comprises a sidewall inclined at 45° with respect to the upper surface 3 of the support. However, the microstructured patterns could have more complex shapes as shown in reference to FIG. 2a.

Each microstructured pattern can be made from one of the following materials: polycarbonate, acrylic resin, polymer with a polystyrene (PS), poly hydroxy styrene (PHS), or poly methyl methacrylate (PMMA) base.

Moreover, each microstructured pattern has in an embodiment a height substantially equal to the height of the trench in which it is located.

These optical systems 12 therefore make it possible to direct the incident light in the cavities 11 and they also make it possible to collect the Raman signal emitted by the molecules that will be deposited on the surface of the substrate.

Figure 1F:
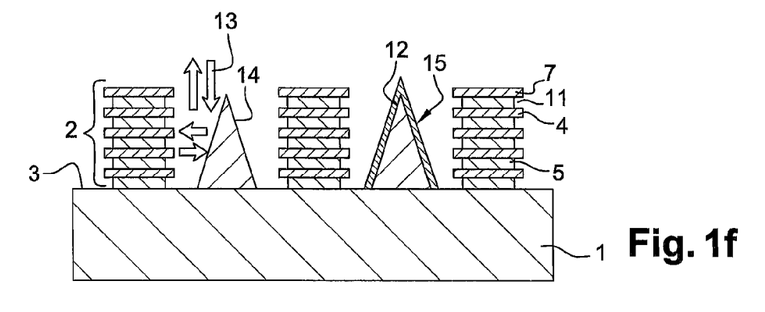

In reference to FIG. 1f, the method can also comprise a step of depositing a reflective layer 15 on each microstructured pattern in such a way as to increase the quantity of incident light directed in the cavities 11 and to increase the quantity of the Raman signal collected. The reflective layer 15 is in an embodiment chosen to be reflective at the wavelength of the incident light in such a way as to prevent the losses of intensity in the material in order to manufacture these structures. As such, according to an embodiment, the reflective layer can be constituted of a layer of one or several of the following materials: Al, Ti, TiN, Au, Ag. According to a second embodiment, the reflective layer can be constituted of a multilayer of dielectrics, such as for example SiO2/Si3N4. This second embodiment makes it possible to form a Bragg mirror of high reflectivity. The reflective layer can for example be deposited by PVD, EVAP or electrodeposition.

The method can then comprise a step of depositing molecules to be detected on the surface of the substrate formed as such.

Figure 3A:
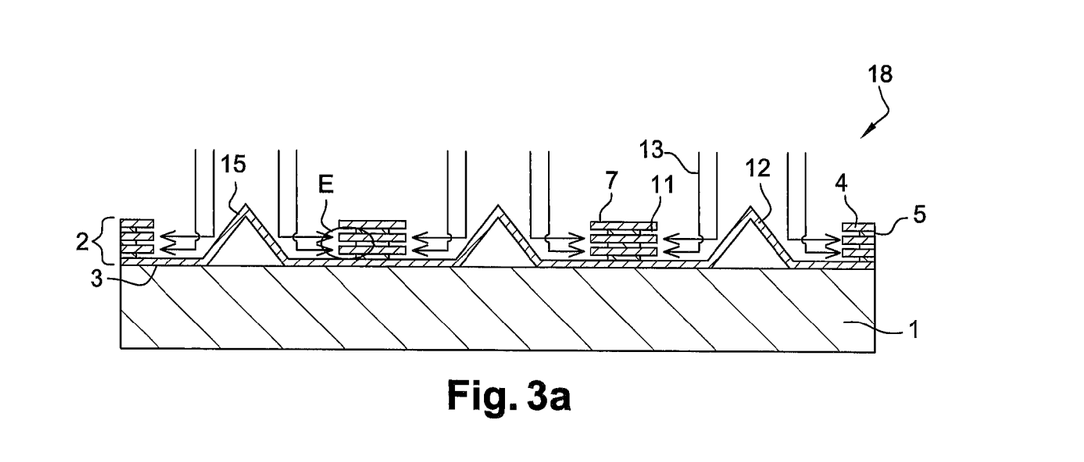
FIGS. 3a and 3b, a substrate according to an embodiment of the invention.
Figure 3B:
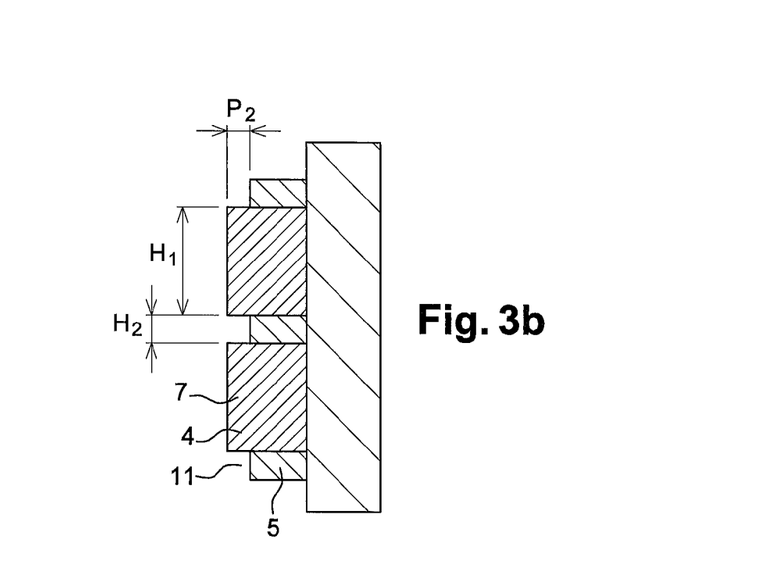

A substrate 18 such as shown in FIGS. 3a and 3b is as such obtained which improves the Raman excitation of the molecules to be detected and which makes it possible as such to improve the signal-to-noise ratio of the measurement. Furthermore, the substrate obtained as such is easy to manufacture and it has dimensions that are easy to control.

Figure 2B:
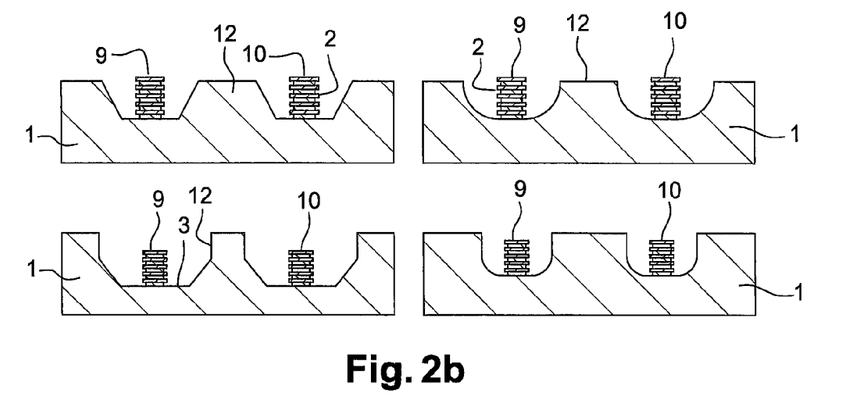

The method is not limited to the steps described in reference to the figures and alternatives can be considered without leaving the scope of the invention. As such, in the method described in reference to FIGS. 1a to 1f, the optical systems are carried out after the steps 101 to 103 of forming the metal pins separated by cavities. However, as shown in reference to FIGS. 2a and 2b, it can also be considered to first carry out the optical systems 12 on the surface of the support 1, and then to form segments 9, 10 of multilayer 2 between these optical systems 12. In this case, the microstructured patterns forming the optical systems can be carried out by etching directly the upper surface of the support, in such a way that the microstructured patterns are carried out using a portion of the support which is etched in such a way as to have the geometry sought. The multilayer is then deposited on the surface of the microstructured support, then the multilayer is etched in such a way as to carry out the trenches on microstructured patterns and to retain multilayer segments between two successive microstructured patterns.

Dimensioning of the Metal Pins and of the Cavities:

A method for dimensioning metal pins 7 and the cavities 11 shall now be described in reference to FIGS. 3a and 3b.

The dimensions chosen for the pins and the cavities are essential in order to obtain a resonance of the electromagnetic field. These dimensions can be determined according to the method explained hereinafter.

The length of the incident wavelength of the incident light that will be sent is first chosen on the molecules to be detected. This incident wavelength can be chosen according to the molecules to be detected and/or according to the equipment available to the user. In this embodiment, an incident wavelength of 785 nm for example is chosen.

Then the materials are chosen that will constitute the metal layers and the intermediate layers of the multilayer 2. These materials can be chosen according to the methods of depositing available, and/or for reasons of chemical affinities with the molecules to be detected, and/or according to the absorption properties of these materials with regards to the incident wavelength. In this embodiment, it is chosen for example to carry out metal layers made of gold and intermediate layers made of $SiO_2$.

The method then comprises a step of dimensioning cavities 11 and metal pins 7 according to the incident wavelength chosen and materials chosen for the multilayer. Indeed, it is possible to determine the dimensions of the pins and of the cavities in such a way that the substrate has a resonance at the wavelength of the incident light. For this, the dimensions of the cavities 11 and of the pins 7 are determined that minimise the reflectivity of the substrate and therefore which maximise the reinforcing of the electromagnetic field when the incident light illuminates a surface perpendicular to the upper surface 3 of the substrate. A method called RCWA (rigorous coupled wave analysis) or a method called FDTD for "finite difference time domain" can for example be used for this. These methods make it possible to simulate the reflectivity of a surface according to its geometry and its composition.

These methods make it possible to determine the dimensions that minimise the reflectivity of the substrate and that maximise the electromagnetic field locally. These are in particular the following dimensions:

the thickness H1 of each metal pin, and therefore the thickness H1 of each metal layer deposited;
the thickness H2 of each cavity, and therefore the thickness H2 of each intermediate layer deposited;
the depth P2 of each cavity;
the number of layers in the multilayer.

Naturally the invention is not limited to the embodiments described and alternatives can be considered without leaving the scope of the invention.

The invention claimed is:

1. A method for manufacturing a substrate for surface-enhanced Raman spectography, the method comprising:
   (a) depositing a multilayer on an upper surface of a support, with the multilayer comprising at least two metal layers separated from each other by an intermediate layer, the intermediate layer able to be selectively etched with respect to the metal layers;
   (b) etching the multilayer in such a way as to form at least one trench through the multilayer, with the trench being delimited by ends of each one of the layers of the multilayer;
   (c) selective etching a portion of each end of each intermediate layer in such a way as to form a cavity between the ends of two successive metal layers in such a way that the ends of two successive metal layers form metal pins separated by a cavity;
   (d) forming a reflective optical system in each trench, with the reflective optical system being arranged to direct inside the cavities an incident light arriving according to an angle with respect to the upper surface of the support without producing any surface-enhanced Raman spectrography, wherein the step (d) of forming the optical system comprises forming a microstructured pattern protruding from the upper surface of the support.

2. The method according to claim 1, wherein the steps (a), (b) and (c) take place before the step (d).

3. The method according to claim 1, wherein the step (b) of etching the multilayer comprises:
   depositing a resin on the multilayer;
   etching the resin by lithography;
   etching the multilayer by dry etching.

4. The method according to claim 1, wherein the step (d) of forming the optical system comprises depositing a reflective layer on the microstructured pattern.

5. The method according to claim 1, wherein the trench is formed only after forming the multilayer on the upper surface of the support.

6. The method according to claim 1, wherein the etching of step (b) is carried out through an entire thickness of the multilayer.

7. The method according to claim 1, wherein the reflective optical system and the multilayer are made of different materials.

8. The method according to claim 7, wherein the reflective optical system is made from one of the following materials: polycarbonate, acrylic resin, polymer with a polystyrene (PS), poly hydroxy styrene (PHS), or poly methyl methacrylate (PMMA) base.

9. A substrate for surface-enhanced Raman spectography comprising:
   a support comprising an upper surface;
   a multilayer deposited on the upper surface of the support, with the multilayer comprising at least two metal layers separated from each other by an intermediate layer, the intermediate layer able to be selectively etched with respect to the metal layers, with the multilayer being passed through by at least one trench delimited by ends of each one of the layers of the multilayer, each end of each intermediate layer being set back with respect to the end of each metal layer adjacent to the intermediate layer in such a way that the ends of two successive metal layers form metal pins separated by a cavity; and
   a reflective optical system arranged in each trench, with the reflective optical system being arranged to direct inside the cavities an incident light arriving according to an angle with respect to the upper surface of the support without producing any surface-enhanced Raman spectrography, wherein the optical system comprises a microstructured pattern protruding from the upper surface of the support.

10. The substrate according to claim 9, wherein the multilayer extends parallel to the surface of the support.

11. The substrate according to claim 9, wherein each trench extends according to a direction normal to the surface of the support.

12. The substrate according to claim 9, wherein each cavity extends according to a direction parallel to the upper surface of the support.

13. The substrate according to claim 9, wherein the microstructured pattern is covered with a reflective layer.

14. The substrate according to claim 9, wherein the reflective optical system and the multilayer are made of different materials.

15. The substrate according to claim 14, wherein the reflective optical system is made from one of the following materials: polycarbonate, acrylic resin, polymer with a polystyrene (PS), poly hydroxy styrene (PHS), or poly methyl methacrylate (PMMA) base.

* * * * *